(12) United States Patent
Nakazawa

(10) Patent No.: US 7,569,548 B2
(45) Date of Patent: Aug. 4, 2009

(54) METHOD OF PREPARING PEPTIDE

(75) Inventor: Masakazu Nakazawa, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 484 days.

(21) Appl. No.: 11/073,729

(22) Filed: Mar. 8, 2005

(65) Prior Publication Data

US 2005/0203028 A1     Sep. 15, 2005

(30) Foreign Application Priority Data

Mar. 9, 2004     (JP)     ............... 2004-066256

(51) Int. Cl.
*A61K 38/06*     (2006.01)
*A61K 38/24*     (2006.01)

(52) U.S. Cl. .................. 514/18; 530/331; 530/313

(58) Field of Classification Search ............ None
See application file for complete search history.

(56) References Cited

U.S. PATENT DOCUMENTS

| | | | |
|---|---|---|---|
| 5,212,288 A | | 5/1993 | Nestor, Jr. et al. |
| 5,322,931 A | * | 6/1994 | Hubbs et al. ............... 530/333 |
| 5,710,247 A | * | 1/1998 | Funk et al. ................. 530/327 |
| 5,843,901 A | * | 12/1998 | Roeske ....................... 514/15 |
| 6,235,876 B1 | * | 5/2001 | Palmer et al. ............... 530/330 |
| 6,492,490 B1 | | 12/2002 | Abdel-Magid et al. | |

FOREIGN PATENT DOCUMENTS

| | | | |
|---|---|---|---|
| EP | 0 301 850 A2 | | 2/1989 |
| EP | 0 328 090 A2 | | 8/1989 |
| WO | WO 97/34924 | * | 9/1997 |
| WO | WO 99/26964 | | 6/1999 |
| WO | WO 03/055902 | * | 7/2003 |
| WO | WO 03/055902 A1 | | 7/2003 |

OTHER PUBLICATIONS

Abdel-Magid, 1998, Tetrahedron Letters, 39, 3391-3394.*
Aleksander M. Kolodziejczyk et al. "Effect of tertiary amines and amine salts on racemization in peptide synthensis", Int. J. Peptide Protein Res. 28, 1986, pp. 444-449.
Adrian Thaler et al; "Lithium-Salt Effects in Peptide Synthesis", Helvetica Chimica Acta—vol. 74, 1991, pp. 617-627.
J.J. Nestor, Jr., et al., "Synthesis and Biological Activity of Some Very Hydrophobic Superagonist Analogues of Luteinizing Hormone-Releasing Hormone", J. Med. Chem., vol. 25, No. 7, 1982, pp. 795-801, XP-001074073.

* cited by examiner

*Primary Examiner*—Andrew D Kosar
*Assistant Examiner*—Satyanarayana R Gudibande
(74) *Attorney, Agent, or Firm*—Oblon, Spivak, McClelland, Maier & Neustadt, P.C.

(57) ABSTRACT

The present invention provides a method of preparing an intermediate for LHRH antagonists, which requires fewer steps than conventional methods and provides the intermediate in high yield and high purity.

20 Claims, No Drawings

METHOD OF PREPARING PEPTIDE

CROSS-REFERENCE TO RELATED APPLICATIONS

The present application claims priority to Japanese application number JP 2004-066256, filed on Mar. 9, 2004, which is hereby incorporated by reference in its entirety.

BACKGROUND OF THE INVENTION

1. Field of the Invention

The present invention provides a method for preparing a peptide. In particular, the present invention provides a method of making an intermediate for preparation of Luteinizing Hormone-Releasing Hormone (hereinafter also referred to as "LHRH") antagonists.

2. Discussion of the Background

Heretofore, several LHRH antagonists have been identified, which include:

Cetrolelix:
Ac-D-2Nal-D-4ClPhe-D-3Pal-Ser-Tyr-D-Cit-Leu-Arg-Pro-D-Ala-NH$_2$;

Antarelix:
Ac-D-2Nal-D-4ClPhe-D-3Pal-Ser-Tyr-Hci-Leu-Lys(iPr)-Pro-D-Ala-NH$_2$;

Abarelix:
Ac-D-2Nal-D-4ClPhe-D-3Pal-Ser-Tyr(NCH$_3$)-D-Asn-Leu-Lys(iPr)-Pro-D-Ala-NH$_2$;

Ganirelix:
Ac-D-2Nal-D-4ClPhe-D-3Pal-Ser-Tyr-D-Lys(C(NHEt)$_2$)-Leu-Lys(C(NHEt)$_2$)-Pro-D-Ala-NH$_2$.

An important intermediate for the aforementioned LHRH antagonists is a tripeptide represented by the formula [I]:

Ac-D-2Nal-D-4ClPhe-D-3Pal-OH     [I]

An example of such a tripeptide is N-acetyl-D-2-naphthylalanyl-D-4-chlorophenylalanyl-D-3-pyridylalanine.

In formula [I], and in the present specification,

"Ac" represents acetyl,

"2Nal" represents a divalent group represented by the formula:

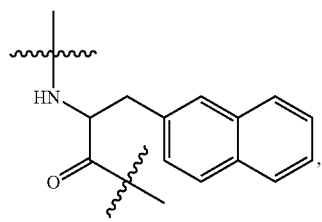

"4ClPhe" represents a divalent group represented by the formula:

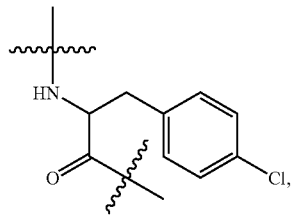

"3Pal" represents a divalent group represented by the formula:

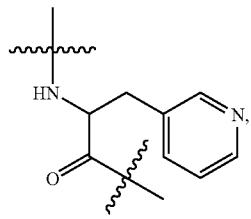

"D" is a prefix for the D-configuration, and
"L" is a prefix for the L-configuration.

In the method of preparing the above-described tripeptide represented by the formula [I], Boc-D-4ClPhe-OH [in the present specification, "Boc" represents a tert-butoxycarbonyl group], for example, is activated by a reaction with N-hydroxysuccinimide, and then condensed with H-D-3Pal-OH 2HCl to yield a dipeptide Boc-D-4ClPhe-D-3Pal-OH. Subsequently, by Boc-deprotection, H-D-4ClPhe-D-3Pal-OH is prepared and is then condensed with Boc-D-2Nal-OH, which was previously separately activated (for example, by a reaction with N-hydroxysuccinimide), to yield Boc-D-2Nal-D-4ClPhe-D-3Pal-OH. Boc-deprotection is performed again and the N-terminal is acetylated to yield the desired tripeptide (see WO 03/055902).

However, because this method employs Boc-D-4ClPhe-OH and Boc-D-2Nal-OH, the Boc group must be deprotected and/or converted to an acetyl group, resulting in an increased number of steps and other problems. Additionally, the Boc-deprotected N-unprotected peptide is highly hygroscopic and hence difficult to handle. Therefore, the purity of the resulting tripeptide is as low as 93.9% (HPLC Area %).

In an alternative synthesis method, Boc-D-4ClPhe-OH and H-D-3Pal-OMe 2HCl are condensed to prepare a dipeptide Boc-D-4ClPhe-D-3Pal-OMe, which is Boc-deprotected and then condensed with Boc-D-2Nal-OH to yield the tripeptide Boc-D-2Nal-D-4ClPhe-D-3Pal-OMe (85.4% yield) (see WO 97/034924). However, to obtain the tripeptide represented by the formula [I], the Boc group must be converted to an acetyl group as described above, and the process unavoidably involves a highly hygroscopic N-unprotected peptide.

Still another method is available wherein condensation of Boc-D-2Nal-OH and H-D-4ClPhe-OMe HCl is followed by Boc-deprotection and then acetylation to provide a dipeptide Ac-D-2Nal-D-4ClPhe-OMe (85.7% yield), which dipeptide is used (see WO 99/026964). Again, this method requires the conversion of the protecting group (Boc→Ac), resulting in an increased number of steps. Although it is possible to hydrolyze this dipeptide to yield Ac-D-2Nal-D-4ClPhe-OH (88.0% yield), which can be used to synthesize the tripeptide represented by the formula [I], the D-4ClPhe moiety racemizes, resulting in the contamination of 2.6% of Ac-D-2Nal-L-4ClPhe-OH and an as low purity as 93.7% (HPLC Area %) (see U.S. Pat. No. 6,492,490).

It has generally been reported that racemization often proceeds when using an acetylated amino acid as a starting material (see Int. J. Peptide Protein Res. 28, 1986, 444-449; Helvetica Chimica Acta, 74, 1991, 617-627). As racemization proceeds, a complex extraction step and/or column purification step to remove the diastereomer would be required, resulting in an increased number of steps.

Accordingly, there remains a critical demand for a method of preparing intermediates for LHRH antagonists (i.e., the tripeptide compound represented by the formula [I]) in which the process comprises fewer steps, as well as a method that enables the preparation of the desired intermediate in high yield and high purity.

SUMMARY OF THE INVENTION

It is an object of the present invention to provide a method of preparing the intermediate for synthesis of LHRH antagonists with fewer steps than conventional methods, and in high yield and high purity.

Therefore, to meet the object of the preset invention and to solve the problems existing in the art (supra), the present inventor conducted extensive investigations. As a result thereof, the present inventors have discovered that in the preparation of the intermediate for LHRH antagonists, it is possible to obviate the complex protection-deprotection steps, and also to obviate the extraction steps, column purification steps and the like to remove the diastereomer, by using a compound represented by the formula [II]: Ac-D-2Nal-OH, a salt thereof, or a reactive derivative thereof, as a starting material.

Accordingly, in an object of the present invention is a method of preparing a tripeptide represented by the formula [I]:

Ac-D-2Nal-D-4ClPhe-D-3Pal-OH [I]

or a salt thereof, which comprises at least one of the steps (1) to (4), depending on the starting material:

step (1)—condensing a compound represented by the formula [II]:

Ac-D-2Nal-OH [II]

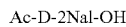

a salt thereof or a reactive derivative thereof, with a compound represented by the formula [III]:

H-D-4ClPhe-OR$^1$ [III]

wherein R$^1$ represents methyl, ethyl or benzyl (preferably methyl), or a salt thereof, to yield a compound represented by the formula [IV]:

Ac-D-2Nal-D-4ClPhe-OR$^1$ [IV]

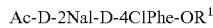

wherein R$^1$ is as defined above;

step (2)—hydrolyzing the compound represented by the formula [IV] to yield a compound represented by the formula [V]:

Ac-D-2Nal-D-4ClPhe-OH [V]

or a salt thereof;

step (3)—condensing the compound represented by the formula [V], a salt thereof or a reactive derivative thereof, with a compound represented by the formula [VI]:

H-D-3Pal-OR$^2$ [VI]

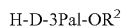

wherein R$^2$ represents methyl, ethyl or benzyl (preferably methyl), or a salt thereof, to yield a compound represented by the formula [VII]:

Ac-D-2Nal-D-4ClPhe-D-3Pal-OR$^2$ [VII]

wherein R$^2$ is as defined above, or a salt thereof; and step (4)—hydrolyzing the compound represented by the formula [VII] or a salt thereof to yield the tripeptide represented by the formula [I] or a salt thereof.

In an embodiment of the present invention as represented by the object above, the reactive derivative of the compound represented by the formula [II] is a compound represented by the formula [IIa]:

Ac-D-2Nal-OR$^a$ [IIa]

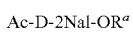

wherein R$^a$ represents a group selected from the group consisting of

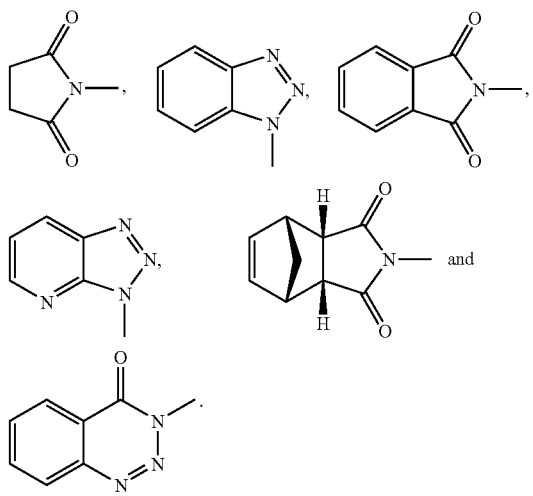

Within an embodiment of the object of the present invention above, the salt of the compound represented by the formula [III] is preferably H-D-4ClPhe-OMe HCl.

Within another embodiment of the object of the present invention above, the salt of the compound represented by the formula [VI] is H-D-3Pal-OMe 2HCl.

In yet another embodiment of the object of the present invention above, the reactive derivative of the compound represented by the formula [V] is a compound represented by the formula [Va]:

Ac-D-2Nal-D-4ClPhe-OR$^a$ [Va]

wherein R$^a$ represents a group selected from the group consisting of

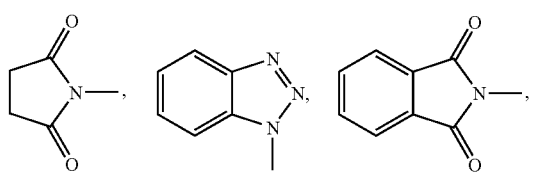

-continued

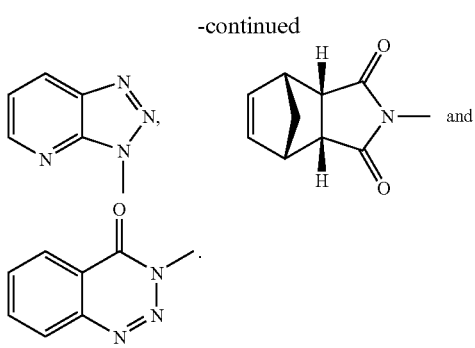

Within an embodiment of the object of the present invention above, a base is used in he hydrolysis reaction of step (2) and/or step (4). In a preferred embodiment the base is sodium hydroxide.

Also within an embodiment of the object of the present invention above, tetrahydrofuran or a mixed solvent of water and tetrahydrofuran is used as a solvent in the hydrolysis reaction of step (2) and/or step (4).

It is another object of the present invention to provide novel methods for preparing a LHRH antagonist(s) by using the tripeptide represented by the formula [I]:

Ac-D-2Nal-D-4ClPhe-D-3Pal-OH  [I]

or a salt thereof produced by the present method.

The above objects highlight certain aspects of the invention. Additional objects, aspects and embodiments of the invention are found in the following detailed description of the invention.

DETAILED DESCRIPTION OF THE INVENTION

Unless specifically defined, all technical and scientific terms used herein have the same meaning as commonly understood by a skilled artisan in chemistry, organic chemistry, medicinal chemistry, and the medical sciences.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

In an embodiment of the present invention is a method of preparing tripeptide [I] or a salt thereof, which includes at least one of steps (1) to (4):

(1) a step of condensing compound [II], a salt thereof or a reactive derivative thereof with compound [III] or a salt thereof to give compound [IV];
(2) a step of subjecting the compound [IV] to a hydrolysis reaction to give compound [V] or a salt thereof;
(3) a step of condensing the compound [V], a salt thereof or a reactive derivative thereof with compound [VI] or a salt thereof to give compound [VII] or a salt thereof; and
(4) a step of subjecting the compound [VII] or a salt thereof to a hydrolysis reaction to give the tripeptide [I] or a salt thereof:

wherein formulae [I]-[VII] are represented by:

| Ac-D-2Nal-D-4ClPhe-D-3Pal-OH | [I] |
| Ac-D-2Nal-OH | [II] |
| H-D-4ClPhe-OR$^1$ | [III] |
| Ac-D-2Nal-D-4ClPhe-OR$^1$ | [IV] |
| Ac-D-2Nal-D-4ClPhe-OH | [V] |
| H-D-3Pal-OR$^2$ | [VI] |
| Ac-D-2Nal-D-4ClPhe-D-3Pal-OR$^2$ | [VII] | and wherein each symbol is as defined in the specification.

As stated above, the present invention for preparing a tripeptide [I] or a salt thereof, "which includes at least one of steps (1) to (4)" means that depending upon the starting Materials selected one or more of the steps may be omitted. For example, if the skilled artisan were in possession of a compound represented by formula [V], a salt thereof or a reactive derivative thereof, then the artisan may start at step (3) of the process rather than at step (1), and so on.

Therefore, in an embodiment of the present invention only step (4) is conducted (i.e., a compound of formula [VII] is used as the starting material).

In another embodiment of the present invention steps (3) and (4) are conducted (i.e., a compound of formula [V] is used as the starting material, which is condensed with a compound of formula [VI]).

In yet another embodiment of the present invention steps (2), (3), and (4) are conducted (i.e., a compound of formula [IV] is used as the starting material).

In still another embodiment of the present invention each of steps (1), (2), (3), and (4) are conducted. Within this embodiment, the method of the present invention may only contain the aforementioned four steps (i.e., a compound of formula [II] is used as the starting material, which is condensed with a compound of formula [III]). Also within this embodiment, the method of the present invention may contain additional steps (e.g., steps for the synthesis of one or more of compounds [II] through [VII]).

The above-described method of preparing the tripeptide represented by the formula [I] (hereinafter also referred to as "tripeptide [I]") or a salt thereof is hereinafter described in detail with reference to the scheme below.

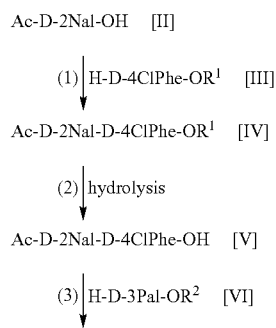

Ac-D-2Nal-D-4ClPhe-D-3Pal-OR²    [VII]

(4) | hydrolysis

Ac-D-2Nal-D-4ClPhe-D-3Pal-OH    [I]

In the scheme above, R¹ represents methyl, ethyl or benzyl, and R² represents methyl, ethyl or benzyl.

As evident from the foregoing, the present method provides a synthetic scheme for making a tripeptide [I] or a salt thereof by only through four steps, i.e., steps (1) to (4). Additionally, the present method does not require extraction, concentration and column purification in each step, and enables the preparation of tripeptide [I] or a salt thereof in high purity and high yield with only separation of the reaction mixture (e.g., filtration etc.) and/or slurry washing.

In the present specification, the salt of tripeptide [I] is not limited, and is exemplified by acid addition salts [for example, salts with inorganic acids (e.g., hydrochloric acid, hydrobromic acid, sulfuric acid, phosphoric acid etc.), salts with organic acids (e.g., formic acid, acetic acid, trifluoroacetic acid, oxalic acid, tartaric acid, citric acid, succinic acid, malic acid, methanesulfonic acid, benzenesulfonic acid, p-toluenesulfonic acid etc.) and the like]; salts with inorganic bases (e.g., alkali metal such as sodium and potassium; alkaline earth metals such as calcium and magnesium; ammonia etc.); and salts with organic bases (e.g., triethylamine, pyridine, picoline, N-methylmorpholine, diisopropylethylamine, cyclohexylamine, dicyclohyxylamine etc.) and the like.

The individual steps are described in detail hereinafter:

Step (1):

Step (1) is a step for a condensation reaction of a compound represented by the formula [II]:

Ac-D-2Nal-OH    [II]

(hereinafter also referred to as Compound [II]), a salt thereof, or a reactive derivative thereof, and a compound represented by the formula [III]:

H-D-4ClPhe-OR¹    [III]

wherein R¹ represents methyl, ethyl or benzyl (hereinafter also referred to as Compound [III]) or a salt thereof.

Although Compound [III] can be synthesized using a method known to those skilled in the art, a commercially available product may also be used.

The reactive derivative of Compound [II] used in the step (1) is not limited, as long as it is obtained from Compound [II] in accordance with a method known to those skilled in the art, such reactive derivatives include, for example, a compound represented by the formula [IIa]:

Ac-D-2Nal-ORᵃ    [IIa]

wherein Rᵃ represents a group selected from the group consisting of

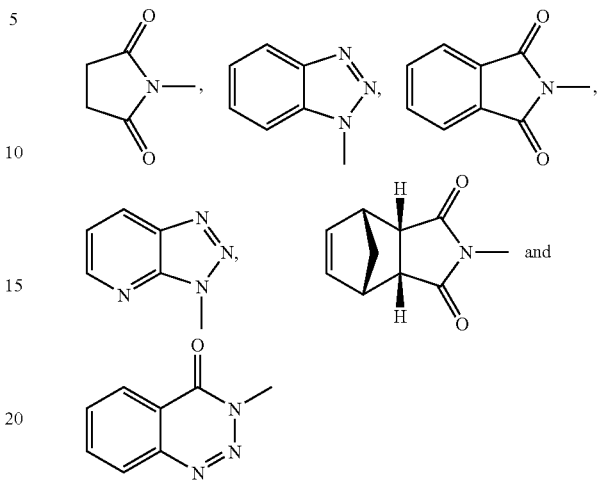

(hereinafter also referred to as Compound [IIa]) and the like.

Compound [IIa] can be readily prepared from Compound [II] by, for example, adding an additive such as N-hydroxysuccinimide (HOSu), 1-hydroxybenzotriazole (HOBt) anhydride or monohydrate, preferably monohydrate, N-hydroxyphthalimide (HOPht), 1-hydroxy-7-azabenzotriazole (HOAt), endo-N-hydroxy-5-norbomene-2,3-dicarboxyimide (HONB) or 3-hydroxy-1,2,3-benzotriazin-4(3H)-one (HOOBt), and a coupling reagent exemplified below, to the reaction system.

The chemical structures of such additives are shown below.

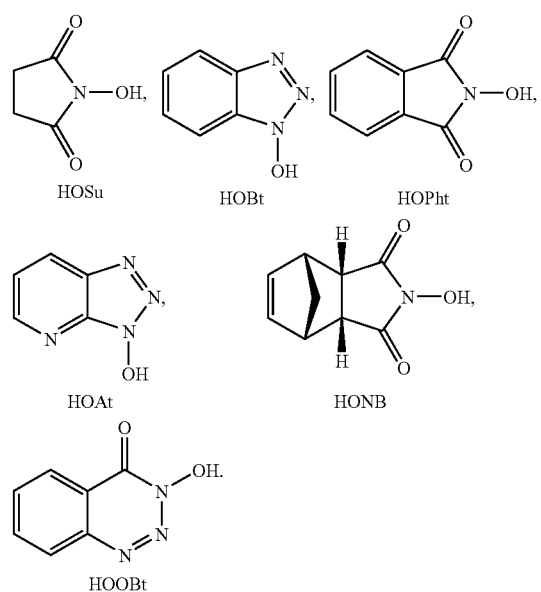

Adding an additive to facilitate preparation of Compound [IIa] to the reaction system offers advantages such as increased reactivity of Compound [II] and suppressed racemization. In particular, from the perspective of racemization suppression, easy removal and costs, HOBt monohydrate is preferred.

The amount of the additive to be added is 0.5 to 2.0 mol, preferably 1.0 to 1.5 mol, and more preferably 1.0 to 1.1 mol, per mol of Compound [II].

The coupling reagents include, but are not limited to, 1,3-dicyclohexylcarbodiimide (DCC), N,N'-diisopropylcarbodiimide (DIPCI) and 1-(3-dimethylaminopropyl)-3-ethylcarbodiimide hydrochloride (EDCI HCl) and the like. However, preference is given to EDCI HCl because the urea derivative by-product can be easily removed following the reaction.

The amount of the coupling reagent to be used is 1.0 to 2.0 mol, preferably 1.0 to 1.5 mol and more preferably 1.0 to 1.1 mol, per mol of Compound [II] or a salt thereof.

Compound [IIa] may be separately prepared in advance.

Salts of Compound [II] include, for example, the salts with inorganic bases and salts with organic bases to exemplify salts of tripeptide [I] mentioned above, and the like.

Although Compound [III] used in the step (1) can be synthesized using a method known to those skilled in the art, a commercially available product may be used.

From the perspective of preparation ease and costs, Compound [III] is preferably H-D-4ClPhe-OMe ($R^1$=methyl).

Salts of Compound [III] include, for example, the acid addition salts to exemplify salts of tripeptide [I] mentioned above and the like, with preference given to hydrochlorides (and more preferably monohydrochloride).

A particularly preferred salt of Compound [III] is H-D-4ClPhe-OMe HCl.

The amount of Compound [III] or a salt thereof to be used is 1.0 to 2.0 mol, preferably 1.0 to 1.5 mol, and more preferably 1.0 to 1.1 mol, per mol of Compound [II], a salt thereof, or a reactive derivative thereof.

Any reaction solvent can be employed, as long as it does not adversely affect the reaction. Examples of suitable solvents include, for example, acetonitrile, tetrahydrofuran (THF), N,N-dimethylformamide (DMF), dichloromethane (DCM), and the like. From the perspective of separation of the product from the diastereomer, additives, coupling reagents and the like, acetonitrile is preferred.

The amount of reaction solvent to be employed is 5 to 50 times, preferably 10 to 30 times, and more preferably 20 to 25 times, as the basis of the weight of Compound [II].

When Compound [III] is a salt, a base such as triethylamine, pyridine, N-methylmorpholine (NMM), or N,N-diisopropylethylamine (DIEA) is further added to the reaction system. In particular, from the perspective of reactivity and costs, triethylamine and NMM are preferred.

The amount of the base to be used is 1.0 to 2.0 mol, preferably 1.0 to 1.5 mol, more preferably 1.0 to 1.1 mol, and still more preferably 1.0 mol, per mol of salt of Compound [III].

The reaction time for step (1) is normally 3 to 48 hours, preferably 6 to 24 hours, and more preferably 8 to 12 hours.

The reaction temperature for step (1) is normally −10 to 40° C., preferably 0 to 25° C., and more preferably 10 to 20° C.

After completion of the reaction, the precipitated crystals are separated (for example, by filtration etc.) and, if necessary, dried (e.g., under reduced pressure at 40° C.), to yield a compound represented by the formula [IV]:

Ac-D-2Nal-D-4ClPhe-OR$^1$     [IV]

wherein $R^1$ as defined above (hereinafter also referred to as Compound [IV]).

After separation, Compound [IV] may be washed with, for example, a solvent such as acetonitrile, tetrahydrofuran, methanol, ethanol, isopropyl alcohol, acetone, or water, or a mixed solvent of water and at least one of these solvents (mixing ratio not limited), and the like.

The amount of the solvent to be used for washing (total amount) is 0.5 to 5 times, preferably 1 to 3 times, and more preferably 2 to 2.5 times, as the basis of the weight of Compound [II].

In step (1), because Compound [II], in which the N-terminal is protected by an acetyl group, or a salt thereof is used as a starting material, protection and deprotection of the N-terminal and conversion of the protecting group to an acetyl group as required in the conventional art is not necessary. Therefore, the present invention can avoid the use of the highly hygroscopic N-unprotected peptide associated with the protection and deprotection of the N-terminal and the conversion of the protecting group. Additionally, racemization proceeds in step (1), resulting in the production of the diastereomer: Ac-L-2Nal-D-4ClPhe-OR$^1$ during the procedure. However, this diastereomer appears in up to 2 to 4 area % relative to Compound [IV] and is completely removed to the mother liquor by separation (e.g., filtration etc.), so that Compound [IV] is obtained in high purity and high yield (purity not less than 99.0 area %, 90.0 to 93.0% yield).

Therefore, in the step (1), conventionally required extraction, concentration and column purification to remove the diastereomer are obviated, so that the total number of the steps can be reduced.

The unit "area %" is the percentage of a peak area ratio in HPLC (high performance liquid chromatography).

In the step (1), the HPLC system was operated under the conditions shown below. Column: Inertsil ODS-2 (4.6×150 mm), eluent: a mixture of 0.05M $KH_2PO_4$ (pH 3) and $CH_3CN$ (60:40), wavelength: 210 nm, flow rate: 1.0 ml/min, temperature: room temperature (about 15 to 25° C.).

Step (2):

Step (2) is a step wherein Compound [IV] is hydrolyzed to yield a compound represented by the formula [V]:

Ac-D-2Nal-D-4ClPhe-OH     [V]

(hereinafter also referred to as Compound [V]) or a salt thereof.

Salts of Compound [V] include, for example, the salts with inorganic bases and salts with organic bases to exemplify salts of tripeptide [I] mentioned, above and the like.

Any solvent can be used in the step (2), as long as it does not adversely affect the reaction, and such solvents include, for example, organic solvents such as methanol, tetrahydrofuran, acetone, and N,N-dimethylformamide, and mixed solutions of water and at least one of these organic solvents, and the like. From the viewpoint of reaction rate and racemization suppression, tetrahydrofuran is preferred.

When a mixed solvent of water and at least one of the aforementioned organic solvents is used, their mixing ratio (organic solvent:water) is not limited, but is normally 99:1 to 1:99 (v/v), preferably 20:80 to 70:30 (v/v), and more preferably 40:60 to 50:50 (v/v).

The amount of the solvent to be employed (total amount) is 5 to 30 times, preferably 10 to 20 times, and more preferably 10 to 15 times, as the basis of the weight of Compound [IV].

The hydrolysis reaction in the step (2) is preferably performed in the presence of a base. The presence of a base is advantageous because a deacetylation reaction can proceed under acidic conditions.

Bases for use in the present invention include, for example, sodium hydroxide, potassium hydroxide, and lithium hydroxide and the like. In particular, from the viewpoint of costs, sodium hydroxide is preferred.

The amount of the base to be used is 1.0 to 2.0 mol, preferably 1.0 to 1.5 mol, more preferably 1.0 to 1.1 mol, and still more preferably 1.05 mol, per mol of Compound [IV].

An aqueous solution of the base may be used. In preparing an aqueous solution of the base, the amount of water to be used is 0.2 to 5 L, preferably 0.4 to 2 L, and more preferably 0.5 to 1 L, per mol of the base.

The reaction time for step (2) is normally 2 to 24 hours, preferably 4 to 18 hours, and more preferably 6 to 12 hours.

The reaction temperature for step (2) is normally −20 to 50° C., preferably −20 to 20° C., and more preferably 0 to 5° C.

After completion of the hydrolysis reaction, a volume of water 1 to 3 times, preferably 1.5 times relative to the volume of the organic solvent used in the reaction is added, and the mixture is generally adjusted to pH 4.0 to 1.0, preferably 2.5 to 1.5, and more preferably 2, by the addition of an acid, to crystallize Compound [V].

The acids for use in the aforementioned acid addition include, for example, hydrochloric acid and sulfuric acid and the like. The concentration and the amount of the acid to be used are not limited, as long as the above-described pH range can be accomplished.

By separating (e.g., filtration etc.) and, if necessary, drying (e.g., under reduced pressure at 40° C.) the precipitated crystals, Compound [V] can be obtained in high purity and high yield (purity not less than 98.0 area %, 93 to 98% yield). The obtained Compound [V] may be converted to the salts with inorganic bases or organic bases to exemplify salts of tripeptide [I] mentioned above according to a known method and the like.

After the above-described separation (but before drying), Compound [V] may be washed with, for example, a solvent such as tetrahydrofuran, methanol, ethanol, isopropyl alcohol, acetone, or water, or a mixed solvent of water and at least one of these solvents (mixing ratio not limited).

The amount of the solvent to be used for washing (total amount) is 0.5 to 5 times, preferably 1 to 3 times, and more preferably 2 to 2.5 times, as the basis of the weight of Compound [IV].

In the step (2), racemization proceeds, resulting in the production of the diastereomer: Ac-D-2Nal-L-4ClPhe-OH. However, this diastereomer appears in up to 0.5 to 1.0 area % relative to Compound [V], so that after separation and washing, Compound [V] is obtained in high purity and high yield (purity not less than 99.0 area %, 93.0 to 98.0% yield).

Therefore, in the step (2) as well, extraction, concentration and column purification to remove the diastereomer are not necessay, so that the total number of the steps can be reduced.

In the step (2), the HPLC system was operated under the conditions shown below. Column: Inertsil ODS-2 (4.6×150 mm), eluent: a mixture of 0.05M $KH_2PO_4$ (pH 3) and $CH_3CN$ (65:35), wavelength: 210 nm, flow rate: 1.0 ml/min, temperature: room temperature (about 15 to 25° C.).

Step (3):

Step (3) is a step for condensation of Compound [V], a salt thereof, or a reactive derivative thereof, and a compound represented by the formula [VI]:

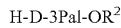          [VI]

wherein $R^2$ represents methyl, ethyl or benzyl (hereinafter also referred to as Compound [VI]) or a salt thereof.

The reactive derivative of Compound [V] for use in the step (3) is not limited, as long as it can be derivatized from Compound [V] according to a method known to those skilled in the art, and is exemplified by a compound represented by the formula [Va]:

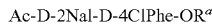          [Va]

wherein $R^a$ is as defined above, and may be independently identical to $R^a$ in the aforementioned Compound [IIa], or not (hereinafter also referred to as Compound [Va]) and the like.

Compound [Va] can easily be prepared from Compound [V], by, for example, adding an additive such as HOSu, HOBt anhydride or monohydrate, preferably monohydrate, HOPht, HOAt, HONB, or HOOBt, and a coupling reagent exemplified below, to the reaction system.

Adding the additive mentioned above to the reaction system offers advantages such as increased reactivity of Compound [V] and suppressed racemization. In particular, from the viewpoint of racemization suppression, easy removal and costs and the like, HOBt monohydrate is preferred.

The amount of the additive to be used is 0.5 to 2.0 mol, preferably 1.0 to 1.5 mol, and more preferably 1.0 to 1.2 mol, per mol of Compound [V].

The coupling reagents include, for example, DCC, DIPCI, and EDCI HCl and the like, with preference given to EDCI HCl because of ease of removing the urea derivative as byproducts after the reaction.

The amount of the coupling reagent to be used is 1.0 to 2.0 mol, preferably 1.0 to 1.5 mol, and more preferably 1.0 to 1.1 mol, per mol of Compound [V] or a salt thereof.

Compound [Va] may be separately prepared in advance.

Salts of Compound [V] include, for example, the salts with inorganic bases and salts with organic bases to exemplify salts of tripeptide [I] mentioned above, and the like.

Although Compound [VI], used in the step (3), can be synthesized using a method known to those skilled in the art, a commercially available product may be used.

From the perspectve of ease of preparation and costs, Compound [VI] is preferably H-D-3Pal-OMe ($R^2$=methyl).

Salts of Compound [VI] include, for example, the acid addition salts to exemplify salts of tripeptide [I] mentioned above, and the like, with preference given to hydrochlorides (and more preferably dihydrochloride).

A particularly preferred salt of Compound [VI] is H-D-3Pal-OMe 2HCl.

The amount of Compound [VI] or a salt thereof to be used is 1.0 to 1.5 mol, preferably 1.0 to 1.2 mol, and more preferably 1.0 to 1.1 mol, per mol of Compound [V], a salt thereof, or a reactive derivative thereof.

Any reaction solvent may be used, as long as it does not adversely affect the reaction; such solvents include, for example, acetonitrile, tetrahydrofuran (THF), N,N-dimethylformamide (DMF), dichloromethane (DCM) and the like. From the viewpoint of ease of isolation of the product, costs, and optical purity, acetonitrile and DMF are preferred, and acetonitrile is particularly preferred.

The amount of reaction solvent to be used is 5 to 50 times, preferably 10 to 40 times, and more preferably 25 to 30 times, as the basis of the weight of Compound [V].

Furthermore, it is preferable to add a base such as triethylamine, pyridine, NMM, or DIEA to the reaction system, in particular, from the viewpoint of reactivity and costs, triethylamine is preferred.

The amount of the base to be used is 1.0 to 2.0 mol, preferably 1.0 to 1.5 mol, more preferably 1.0 to 1.05 mol, and still more preferably 1.0 mol, per mol of Compound [VI].

When Compound [VI] is a salt, the amount of the base to be used is 2.0 to 4.0 mol, preferably 2.0 to 3.0 mol, more preferably 2.0 to 2.1 mol, and still more preferably 2.0 mol, per mol of the salt of Compound [VI].

The reaction time for step (3) is normally 3 to 48 hours, preferably 6 to 24 hours, and more preferably 8 to 18 hours.

The reaction temperature for step (4) is normally −10 to 40° C., preferably 0 to 25° C., and more preferably 10 to 20° C.

After completion of the reaction, it is preferable to add a volume of water equal to the volume of DMF used to the reaction system when the solvent is DMF.

After completion of the reaction, the precipitated crystals are separated (e.g., filtration etc.) to yield a compound represented by the formula [VII]:

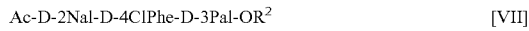

Ac-D-2Nal-D-4ClPhe-D-3Pal-OR$^2$      [VII]

wherein R$^2$ as defined above (hereinafter also referred to as Compound [VII]) or a salt thereof. Salts of Compound [VII] include, for example, the acid addition salts to exemplify salts of tripeptide [I] mentioned above, and the like.

After separation, Compound [VII] or a salt thereof may be washed with, for example, a solvent such as acetonitrile, tetrahydrofuran, methanol, ethanol, isopropyl alcohol, acetone, or water, or a mixed solvent of water and at least one of these solvents (mixing ratio not limited), and the like.

The amount of the solvent to be used for washing (total amount) is 1 to 15 times, preferably 2 to 10 times, and more preferably 4 to 5 times, as the basis of the weight of Compound [V] or a salt thereof.

Compound [VII] obtained in the above-described step sometimes contains the diastereomer: Ac-D-2Nal-L-4ClPhe-D-3Pal-OR$^2$, however, this diastereomer appears in not more than 1.0 area % relative to Compound [VII] (but not more than 0.5 area % when the reaction solvent is acetonitrile).

In step (3), the HPLC system was operated under the conditions shown below. Column: Inertsil ODS-2 (4.6×150 mm), eluent: a mixture of 0.05M KH$_2$PO$_4$ (pH 3) and CH$_3$CN (65:35), wavelength: 210 nm, flow rate: 1.0 ml/min, temperature: room temperature (about 15 to 25° C.).

Further, it is possible to remove the undesirable diastereomer to the mother liquor using a separation technique such as filtration, whereby Compound [VII] or a salt thereof is obtained in high purity and high yield. The thus-obtained Compound [VII] or a salt thereof can be subjected to slurry washing to achieve purification more conveniently and more efficiently.

Slurry washing of Compound [VII] or a salt thereof is conducted using an organic solvent such as methanol, tetrahydrofuran, acetone, or DMF, or a mixed solution of water and at least one of the aforementioned organic solvents, preferably using a mixed solvent of water and tetrahydrofuran. When a mixed solvent of water and at least one of the aforementioned organic solvents is used, their mixing ratio (organic solvent:water) is not limited, and is normally 2:1 to 1:2 (v/v), preferably 1:1 to 1:3 (v/v), and more preferably 3:4 (v/v).

The amount of the solvent to be used (total amount) is 10 to 40 times, preferably 15 to 30 times, and more preferably 20 to 25 times, as the basis of the weight of Compound [V] or a salt thereof.

The pH during slurry washing is normally 6 to 10, preferably 7.0 to 9.0, and more preferably 8.0 to 8.5.

In order to adjust the pH, a base, for example, sodium hydrogen carbonate, sodium carbonate, potassium hydrogen carbonate, or potassium carbonate and the like, is used, which base is preferably used in an aqueous solution. The concentration and the amount of the base to be used are not limited, as long as the above-described pH range can be obtained.

By separating (e.g., filtration etc.) and, if necessary, drying (e.g., under reduced pressure at 40° C.) the crystals obtained by the slurry washing, Compound [VII] or a salt thereof can be obtained in even higher purity and higher yield (purity not less than 98.0 area %, 75 to 90% yield). After slurry washing, the diastereomer: Ac-D-2Nal-L-4ClPhe-D-3Pal-OR$^2$ appears in not more than 0.2 area % (but not more than 0.1 area % when the reaction solvent is acetonitrile).

Furthermore, after the above-described separation (but before drying), Compound [VII] or a salt thereof may be further washed with, for example, a solvent such as tetrahydrofuran, acetonitrile, methanol, ethanol, isopropyl alcohol, acetone, or water, or a mixed solvent of water and at least one of these solvents (mixing ratio not limited), and the like.

The amount of the solvent to be used for washing (total amount) is 1 to 4 times, preferably 1.5 to 3 times, and more preferably 2 to 2.5 times, as the basis of the weight of Compound [V] or a salt thereof.

Purification of Compound [VII] or a salt thereof is achieved by filtration and/or slurry washing. Therefore, extraction, concentration and column purification to remove the diastereomer, which are required steps in the conventional methods employed in the art are unnecessary, so that the total number of the steps can be reduced.

Step (4):

Step (4) is a step wherein Compound [VII] or a salt thereof is hydrolyzed to yield tripeptide [I] or a salt thereof.

Any solvent can be used in the step (4), as long as it does not adversely affect the reaction. Acceptable solvents include, for example, organic solvents such as methanol, tetrahydrofuran, acetone, and N,N-dimethylformamide, and mixed solutions of water and at least one of these organic solvents, and the like. From the perspective of reaction temperature and racemization suppression, a mixed solvent of water and tetrahydrofuran is preferred.

When a mixed solvent of water and at least one of the aforementioned organic solvents is used, their mixing ratio (organic solvent:water) is not limited, and is normally 2:1 to 1:4 (v/v), preferably 1:1 to 1:3 (v/v), and more preferably 1:1 (v/v).

The amount of the solvent to be used (total amount) is 10 to 50 times, preferably 20 to 40 times, and more preferably 30 to 35 times, as the basis of the weight of Compound [VII] or a salt thereof.

The hydrolysis reaction in the step (4) is preferably performed in the presence of a base. The preference for the presence of a base derives from the fact that a deacetylation reaction can proceed under acidic conditions. Suitable bases include, for example, sodium hydroxide, potassium hydroxide, and lithium hydroxide and the like. In particular, from the viewpoint of costs, sodium hydroxide is preferred.

The amount of the base to be employed is 1.0 to 2.0 mol, preferably 1.0 to 1.5 mol, more preferably 1.0 to 1.1 mol, and still more preferably 1.05 mol, per mol of Compound [VII] or a salt thereof.

An aqueous solution of the base may also be used. In preparing the aqueous solution of the base, the amount of water to be used is 0.2 to 5 L, preferably 0.4 to 2 L, and more preferably 0.5 to 1 L, per mol of the base.

The reaction time for step (4) is normally 4 to 48 hours, preferably 6 to 24 hours, and more preferably 12 to 18 hours.

The reaction temperature for step (4) is normally −20 to 40° C., preferably −10 to 20° C., and more preferably 0 to 5° C.

After completion of the hydrolysis reaction, a volume of water 0.5 to 1 times, preferably 0.5 times, relative to the volume of the organic solvent used in the reaction is added, and the pH of the mixture is adjusted to a pH of normally 4 to 6, preferably 4.5 to 5.5, and more preferably 5, by the addition of an acid, to crystallize tripeptide [I] or a salt thereof.

The acids to be used include, for example, hydrochloric acid and sulfuric acid and the like. The concentration and the amount of the acid to be used are not limited, as long as the above-described pH range can be accomplished.

By separating (e.g., filtration etc.) and, if necessary, drying (e.g., under reduced pressure at 50° C.) the precipitated crystals, it is possible to tripeptide [I] or a salt thereof can be obtained in high purity and high yield (purity not less than 99.0 area %, 92 to 97% yield).

Furthermore, after the above-described separation (but before drying), tripeptide [I] or a salt thereof may be washed with, for example, a solvent such as tetrahydrofuran, acetonitrile, methanol, ethanol, isopropanol, acetone, or water, or a mixed solvent of water and at least one of these solvents (mixing ratio not limited).

The amount of the solvent to be used for washing (total amount) is 1 to 10 times, preferably 2 to 8 times, and more preferably 4 to 5 times, as the basis of the weight of tripeptide [VII] or a salt thereof.

In step (4), racemization proceeds and the diastereomer: Ac-D-2Nal-D-4ClPhe-L-3Pal-OH is produced, however, this diastereomer appears in not more than 1.0 area % relative to tripeptide [I] or a salt thereof, and is completely removed to the mother liquor or washings during separation (e.g., filtration etc.) or washing, so that tripeptide [I] or a salt thereof is obtained in high purity and high yield (purity not less than 99.0 area %, 92 to 97% yield).

Therefore, in step (4) as well, extraction, concentration and column purification to remove the diastereomer are unnecessary, so that the total number of the steps can be reduced.

In step (4), the HPLC system was operated under the conditions shown below. Column: Inertsil ODS-2 (4.6×150 mm), eluent: a mixture of 0.05M $KH_2PO_4$ (pH 3) and $CH_3CN$ (70:30), wavelength: 210 nm, flow rate: 1.0 ml/min, temperature: room temperature (about 15 to 25° C.).

Thus, according to the present invention, the intermediate for LHRH antagonists can be obtained with fewer steps than conventional methods, and in high yield and high purity.

In another embodiment, the present invention provides methods for preparing Luteinizing Hormone-Releasing Hormone (hereinafter also referred to as "LHRH") antagonists by converting the tripeptide intermediate represented by the formula [I]:

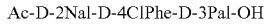   Ac-D-2Nal-D-4ClPhe-D-3Pal-OH   [I]

or a salt thereof, produced by the present method to such a LHRH antagonist. The tripeptide intermediate represented by the formula [I] or salt thereof produced by the present method may be converted to such a LHRH antagonist by the methods described in, e.g., WO 03/055902, WO 97/034924, WO 99/026964, and U.S. Pat. No. 6,492,490, which are incorporated herein in their entireties. Still further, these references also give the skilled artisan an appreciation and enable the production of the full scope of LHRH antagonists in addition to those specifically recited LHRH antagonists in the 'Background of the Invention' (supra).

The above written description of the invention provides a manner and process of making and using it such that any person skilled in this art is enabled to make and use the same, this enablement being provided in particular for the subject matter of the appended claims, which make up a part of the original description.

As used herein, the phrases "selected from the group consisting of," "chosen from," and the like include mixtures of the specified materials.

Further in the method of the present invention, the terms "comprising" and "consisting of" take their usual form and meaning. The term "consisting essentially of" is meant to include the step(s) recited in the claims, which is understood to further encompass the various aspects of each step as defined in the 'Detailed Description of the Invention' (supra).

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

Example 1

N-acetyl-D-2-naphthylalanyl-D-4-chlorophenylalanine methyl ester (Ac-D-2Nal-D-4ClPhe-OMe)

N-acetyl-D-2-naphthylalanine (25.7 g, 0.1 mol) and D-4-chlorophenylalanine methyl ester hydrochloride (25.0 g, 0.1 mol) were suspended in acetonitrile (600 ml), subsequently 1-hydroxybenzotriazole monohydrate (15.3 g, 0.1 mol) was added and the suspension was cooled to 5° C. N-methylmorpholine (11.0 ml, 0.1 mol) and 1-(3-dimethylaminopropyl)-3-ethylcarbodiimide hydrochloride (19.17 g, 0.1 mol) were then added and the suspension was stirred at 5° C. for 1 hour followed by stirring at room temperature overnight. The precipitated crystals were separated and washed with acetonitrile (100 ml). The crystals were dried under reduced pressure at 40° C. to yield 42.0 g of the desired compound. The yield was 92.3%, the purity was 99.53 area %, and the diastereomer was not detected (undetectable).

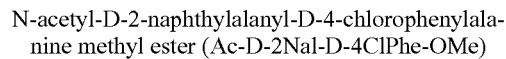
$^1$H-NMR(DMSO-$d_6$) δ(ppm): 1.71(s, 3H), 2.82-2.96(m, 2H), 3.02-3.13(m, 2H),3.54(s, 3H), 4.49(m, 1H), 4.64(m, 1H), 7.23(m, 2H), 7.30(m, 2H), 7.41-7.50(m, 3H), 7.71(s, 1H), 7.81(m, 2H), 7.86(m, 1H), 8.11(m, 1H), 8.51(m, 1H).

Mass spectrum m/e: 451 (MH$^-$)

Example 2

N-acetyl-D-2-naphthylalanyl-D-4-chlorophenylalanine (Ac-D-2Nal-D-4ClPhe-OH)

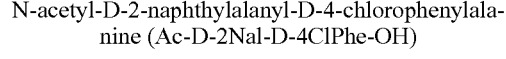
N-acetyl-D-2-naphthylalanyl-D-4-chlorophenylalanine methyl ester (42.0 g, 92.7 mmol) was suspended in THF (460 ml) and the suspension was cooled to 0 to 5° C. A 1M aqueous solution of sodium hydroxide (97.4 mL, 97.4 mmol) was added drop-wise at a temperature of 0 to 5° C. over 30 minutes. The suspension was then stirred at the same temperature for 6 hours until completion of hydrolysis. The temperature was then increased to 15 to 20° C. followed by removal of insoluble materials by filtration. After water (690 ml) was added, the filtrate was adjusted to pH 2 by the addition of 6M hydrochloric acid (19 ml) to facilitate crystallization. The precipitated crystals were subsequently separated and washed with a mixture of THF and water (2:3) (40 ml). The crystals were dried under reduced pressure at 40° C. to yield 40.1 g of the desired compound. The yield was 97.6%, the purity was 99.0 area %, and the diastereomer ratio (DD:DL) was 99.32:0.68.

$^1$H-NMR(DMSO-$d_6$)δ(ppm): 1.71(s, 3H), 2.81-2.96(m, 2H), 3.06-3.16(m, 2H), 4.46(m, 1H), 4.64(m, 1H), 7.25(m, 2H), 7.31(m, 2H), 7.41-7.48(m, 3H), 7.71(s, 1H), 7.79(m, 2H), 7.85(m, 1H), 8.06(m, 1H), 8.33(m, 1H).

Mass spectrum m/e: 437(MH$^-$)

Example 3

N-acetyl-D-2-naphthylalanyl-D-4-chlorophenylalanyl-D-3-pyridylalanine methyl ester (Ac-D-2Nal-D-4ClPhe-D-3Pal-OMe)

N-acetyl-D-2-naphthylalanyl-D-4-chlorophenylalanine (4.39 g, 10 mmol) was suspended in acetonitrile (120 ml), 1-hydroxybenzotriazole monohydrate (1.68 g, 11 mmol) was added, and the suspension was cooled to 5° C. Subsequently, 1-(3-dimethylaminopropyl)-3-ethylcarbodiimide hydrochloride (2.0 g, 10.5 mmol) was added and the suspension was stirred at 5° C. for 1 hour, followed by stirring at room temperature overnight. The suspension was again cooled to 5° C., D-3-pyridylalanine methyl ester dihydrochloride (2.66 g, 10.5 mmol) and triethylamine (2.92 ml, 21 mmol) were added, and the suspension was stirred at room temperature for 4 hours. The precipitated crystals were separated and washed with acetonitrile (20 ml). The diastereomer ratio of the crude crystal (DDD:DLD) was 99.6:0.4. These crude crystals were suspended in water (60 ml) and THF (45 ml), and the pH was adjusted to pH 8 by the addition of a 5% aqueous solution of sodium hydrogen carbonate, and subjected to overnight slurry washing. The crystals were separated and washed with a mixture of THF and water (3:4) (42 ml). The crystals were dried under reduced pressure at 40° C. to yield 5.14 g of the desired compound. The yield was 83.3%, the purity was 98.5 area %, and the diastereomer content was <0.1 area %.

$^1$H-NMR(DMSO-$d_6$)δ(ppm): 1.70(s, 3H), 2.75-2.83(m, 2H), 2.93-2.99(m, 2H), 3.03-3.10(m, 2H), 3.60(s, 3H), 4.53-4.58(m, 3H), 7.23-7.31(m, 5H), 7.38-7.48(m, 3H), 7.63-7.78 (m, 5H), 8.04-8.15(m, 2H), 8.40-8.44(m, 2H), 8.52-8.54(m, 1H).

Mass spectrum m/e: 601(MH$^+$)

Example 4

N-acetyl-D-2-naphthylalanyl-D-4-chlorophenylalanine 1-benzotriazole ester (Ac-D-2Nal-D-4ClPhe-OBt)

N-acetyl-D-2-naphthylalanyl-D-4-chlorophenylalanine (4.39 g, 10 mmol) was suspended in acetonitrile (120 ml), followed by addition of 1-hydroxybenzotriazole monohydrate (1.68 g, 11 mmol), and the resulting suspension was cooled to 5° C. Subsequently, 1-(3-dimethylaminopropyl)-3-ethylcarbodiimide hydrochloride (2.0 g, 10.5 mmol) was added, and the suspension was stirred at 5° C. for 1 hour, followed by stirring at room temperature overnight. The precipitated crystals were separated and washed with acetonitrile (20 mL). The crystals were dried under reduced pressure at room temperature to yield 5.3 g of the desired compound. The yield was 95.3%.

Example 5

N-acetyl-D-2-naphthylalanyl-D-4-chlorophenylalanyl-D-3-pyridylalanine methyl ester (Ac-D-2Nal-D-4ClPhe-D-3Pal-OMe)

D-3-pyridylalanine methyl ester dihydrochloride (0.58 g, 2.1 mmol) was suspended in DMF (20 ml), and the suspension was cooled to 5° C. After N-methylmorpholine (0.46 mL, 4.2 mmol) was added, N-acetyl-D-2-naphthylalanyl-D-4-chlorophenylalanine 1-benzotriazole ester (1.1 g, 2 mmol) was added, and the suspension was stirred at room temperature for 1 hour. Water (20 ml) was then added, and the precipitated crystals were separated. The diastereomer ratio of the crude crystal (DDD:DLD) was 99.4:0.6. These crude crystals were suspended in water (20 ml) and THF (15 ml), and the pH was adjusted to pH 8 by the addition of a 5% aqueous solution of sodium hydrogen carbonate, and subjected to overnight slurry washing. The crystals were separated and washed with a mixture of THF and water (3:4) (14 mL). The crystals were dried under reduced pressure at 40° C. to yield 1.1 g of the desired compound. The yield was 89.3%, the purity was 99.3 area %, and the diastereomer content was 0.2 area %.

Example 6

N-acetyl-D-2-naphthylalanyl-D-4-chlorophenylalanyl-D-3-pyridylalanine methyl ester (Ac-D-2Nal-D-4ClPhe-D-3Pal-OMe)

D-3-pyridylalanine methyl ester dihydrochloride (0.53 g, 2.1 mmol) was suspended in acetonitrile (24 ml), and the suspension was cooled to 5° C. Following addition of triethylamine (0.59 ml, 4.2 mmol), N-acetyl-D-2-naphthylalanyl-D-4-chlorophenylalanine 1-benzotriazole ester (1.1 g, 2 mmol) was added and the suspension was stirred at room temperature for 1 hour. The precipitated crystals were separated. The diastereomer ratio of the crude crystal (DDD:DLD) was 99.6:0.4. These crude crystals were suspended in water (20 ml) and THF (15 ml), and the pH was adjusted to pH 8 by the addition of a 5% aqueous solution of sodium hydrogen carbonate, and subjected to overnight slurry washing. The crystals were separated and washed with a mixture of THF and water (3:4) (14 ml). The crystals were dried under reduced pressure at 40° C. to yield 1.0 g of the desired compound. The yield was 83.2%, the purity was 99.2 area %, and the diastereomer content was not more than 0.1 area %.

Example 7

N-acetyl-D-2-naphthylalanyl-D-4-chlorophenylalanyl-D-3-pyridylalanine (Ac-D-2Nal-D-4ClPhe-D-3Pal-OH)

N-acetyl-D-2-naphthylalanyl-D-4-chlorophenylalanyl-D-3-pyridylalanine methyl ester (2.4 g, 4 mmol) was suspended in THF (40 ml) and water (40 ml), and the suspension was cooled to 0° C. A 1M aqueous solution of sodium hydroxide (4.2 ml, 4.2 mmol) was added, and the suspension was stirred at the same temperature overnight. The temperature was increased to 10° C., and insoluble materials were removed by filtration. After water (20 ml) was added, the filtrate was adjusted to pH 5 by the addition of 6M hydrochloric acid to allow crystallization. The crystals were washed with a mixture of THF and water (1:1) (10 ml) and water (10 ml), respectively. The crystals were dried under reduced pressure at 50° C. to yield 2.27 g of the desired compound. The yield was 96.5%, the purity was 99.8 area %, and the diastereomer content was <0.1 area %.

$^1$H-NMR(DMSO-$d_6$)δ(ppm): 1.69(s, 3H), 2.75-2.83(m, 2H), 2.94-3.12(m, 4H), 4.48-4.60(m, 3H), 7.23-7.29(m, 5H), 7.37-7.47(m, 3H), 7.68-7.78(m, 5H), 8.03-8.13(m, 2H), 8.37-8.46(m, 3H).

Mass spectrum m/e: 586.6(MH$^+$)

As demonstrated by the foregoing Examples, the present invention makes possible a method of preparing intermediates for synthesis of LHRH antagonists with fewer steps than conventional methods. Further, the method of the present invention results in high yields and high purities.

Numerous modifications and variations on the present invention are possible in light of the above teachings. It is, therefore, to be understood that within the scope of the accompanying claims, the invention may be practiced otherwise than as specifically described herein.

The invention claimed is:

1. A method of preparing a diasteromerically pure a tripeptide represented by the formula [I]:

Ac-D-2Nal-D-4ClPhe-D-3Pal-OH  [I]

or a salt thereof, which comprises
hydrolyzing a compound represented by the formula [VII] or a salt thereof in the presence of a solvent to yield the tripeptide represented by the formula [I] or a salt thereof, wherein, said compound represented by the formula [VII] is:

Ac-D-2Nal-D-4ClPhe-D-3Pal-OR$^2$  [VII]

wherein R$^2$ represents methyl, ethyl or benzyl.

2. The method of claim 1, further comprising, prior to said hydrolyzing, at least one of (a) to (c):
(a) condensing a compound represented by the formula [II] or formula [IIa], or a salt thereof, with a compound represented by the formula [III]:

H-D-4ClPhe-OR$^1$  [III]

wherein R$^1$ represents methyl, ethyl or benzyl, or a salt thereof, to yield a compound represented by the formula [IV]:

Ac-D-2Nal-D-4ClPhe-OR$^1$  [IV]

wherein R$^1$ is as defined above,
wherein formula [II] is:

Ac-D-2Nal-OH  [II], and wherein formula [IIa] is:

Ac-D-2Nal-OR$^a$  [IIa]

wherein R$^a$ represents a group selected from the group consisting of

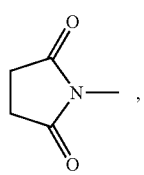, 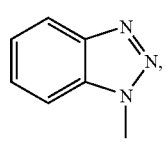

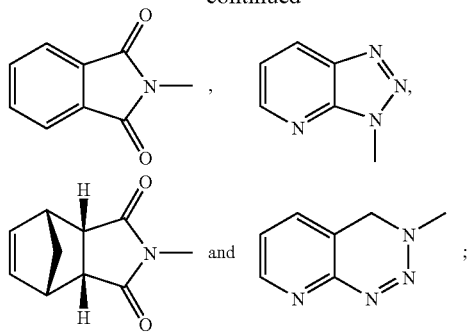

and (b) hydrolyzing the compound represented by the formula [IV] in the presence of a solvent to yield a compound represented by the formula [V] or a compound represented by the formula [Va], or a salt thereof
wherein the compound represented by the formula [V] is:

Ac-D-2Nal-D-4ClPhe-OH  [V]

wherein the compound represented by the formula [Va] is:

Ac-D-2Nal-D-4ClPhe-OR$^a$  [Va]

wherein R$^a$ represents a group selected from the group consisting of

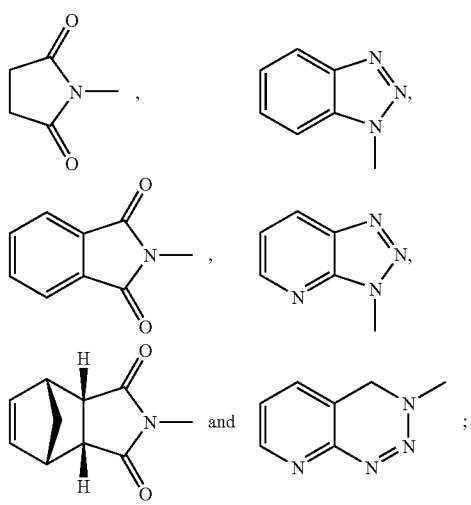

and
(c) condensing the compound represented by the formula [V] or the compound represented by the formula [Va], or a salt thereof, with a compound represented by the formula [VI]:

H-D-3Pal-OR$^2$  [VI]

wherein R$^2$ represents methyl, ethyl or benzyl, or a salt thereof, to yield a compound represented by the formula [VII]:

Ac-D-2Nal-D-4ClPhe-D-3Pal-OR$^2$  [VII]

wherein R$^2$ is as defined above, or a salt thereof.

3. The method of claim 2, wherein said condensing in (a) is with a compound represented by the formula [II] or a salt thereof wherein formula [II] is:

Ac-D-2Nal-OH [II].

4. The method of claim 2, wherein R¹ is methyl.

5. The method of claim 2, wherein the salt of the compound represented by the formula [III] is H-D-4ClPhe-OMe HCl.

6. The method of claim 2, wherein R² is methyl.

7. The method of claim 2, wherein the salt of the compound represented by the formula [VI] is H-D-3Pal-OMe 2HCl.

8. The method of claim 2, wherein the compound yielded in (b) and/or the compound subjected to said condensing in (c) is a compound represented by the formula [V] or a salt thereof wherein the compound represented by the formula [V] is:

Ac-D-2Nal-D-4ClPhe-OH [V].

9. The method of claim 2, wherein a base is used in said hydrolyzing in (b).

10. The method of claim 9, wherein the base is sodium hydroxide.

11. The method of claim 2, wherein tetrahydrofuran is used as a solvent in said hydrolyzing in (b).

12. The method of claim 2, wherein a base is used in said hydrolyzing a compound represented by the formula [VII].

13. The method of claim 12, wherein the base is sodium hydroxide.

14. The method of claim 2, wherein a mixed solvent of water and tetrahydrofuran is used as a solvent in said hydrolyzing a compound represented by the formula [VII].

15. The method of claim 2, wherein said method comprises (c).

16. The method of claim 2, wherein said method comprises (b) and (c).

17. The method of claim 2, wherein said method comprises (a), (b), and (c).

18. The method of claim 2, wherein said method consists essentially of (b) and (c).

19. The method of claim 2, wherein said method consists essentially of (a), (b), and (c).

20. A method of producing a compound represented by the formula [IV], or a salt thereof:

Ac-D-2Nal-D-4ClPhe-OR¹ [IV]

wherein R¹ represents methyl, ethyl or benzyl, wherein said method comprises condensing a compound represented by the formula [II] or formula [IIa], or a salt thereof, with a compound represented by the formula [III]:

H-D-4ClPhe-OR¹ [III]

wherein R¹ represents methyl, ethyl or benzyl, or a salt thereof, wherein formula [II] is:

Ac-D-2Nal-OH [II], and wherein formula [IIa] is:

Ac-D-2Nal-OR^a [IIa]

wherein R^a represents a group selected from the group consisting of

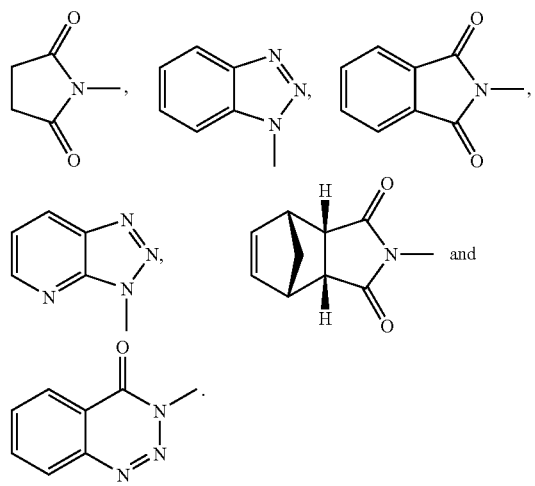

* * * * *

UNITED STATES PATENT AND TRADEMARK OFFICE
CERTIFICATE OF CORRECTION

PATENT NO. : 7,569,548 B2
APPLICATION NO. : 11/073729
DATED : August 4, 2009
INVENTOR(S) : Masakazu Nakazawa It is certified that error appears in the above-identified patent and that said Letters Patent is hereby corrected as shown below:

Column 20, line 46,

Incorrect:

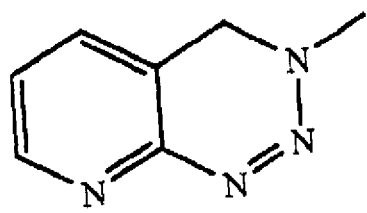

Correct:

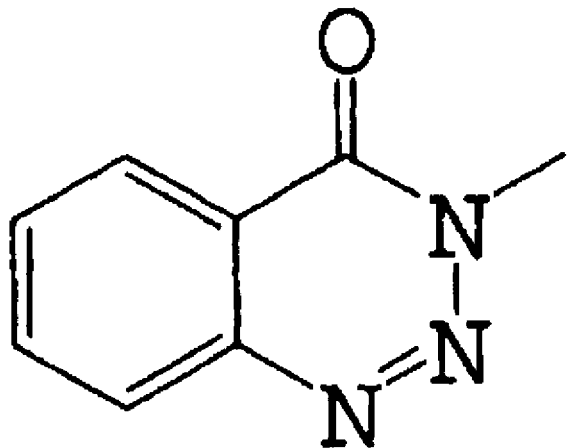

Column 19, line 25, "diasteromerically" should read --diastereomerically--

UNITED STATES PATENT AND TRADEMARK OFFICE
CERTIFICATE OF CORRECTION

PATENT NO. : 7,569,548 B2  
APPLICATION NO. : 11/073729  
DATED : August 4, 2009  
INVENTOR(S) : Masakazu Nakazawa It is certified that error appears in the above-identified patent and that said Letters Patent is hereby corrected as shown below:

Column 20, line 16,

Incorrect:

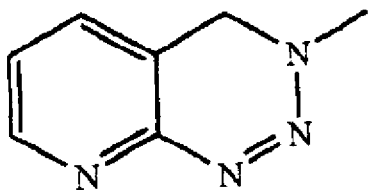

Correct:

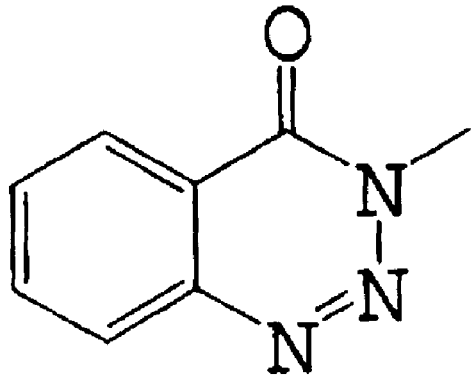

Signed and Sealed this

Fifteenth Day of December, 2009

David J. Kappos  
*Director of the United States Patent and Trademark Office*